US010426869B2

(12) United States Patent
Bhaduri et al.

(10) Patent No.: US 10,426,869 B2
(45) Date of Patent: Oct. 1, 2019

(54) BIODEGRADABLE MAGNESIUM ALLOYS AND COMPOSITES

(71) Applicant: The University of Toledo, Toledo, OH (US)

(72) Inventors: Sarit B. Bhaduri, Toledo, OH (US); Huan Zhou, Toledo, OH (US)

(73) Assignee: The University of Toledo, Toledo, OH (US)

( * ) Notice: Subject to any disclaimer, the term of this patent is extended or adjusted under 35 U.S.C. 154(b) by 296 days.

(21) Appl. No.: 15/308,919

(22) PCT Filed: May 5, 2015

(86) PCT No.: PCT/US2015/029202
§ 371 (c)(1),
(2) Date: Nov. 4, 2016

(87) PCT Pub. No.: WO2015/171585
PCT Pub. Date: Nov. 12, 2015

(65) Prior Publication Data

US 2017/0072103 A1 Mar. 16, 2017

Related U.S. Application Data

(60) Provisional application No. 61/988,512, filed on May 5, 2014.

(51) Int. Cl.

| | |
|---|---|
| ***A61L 27/32*** | (2006.01) |
| ***A61L 27/42*** | (2006.01) |
| ***A61L 27/58*** | (2006.01) |
| ***A61L 29/12*** | (2006.01) |
| ***A61L 29/14*** | (2006.01) |
| ***A61L 31/12*** | (2006.01) |
| ***A61L 31/14*** | (2006.01) |
| ***A61L 29/10*** | (2006.01) |
| ***A61L 31/08*** | (2006.01) |
| ***B22F 1/00*** | (2006.01) |
| ***B22F 3/105*** | (2006.01) |
| ***B22F 3/16*** | (2006.01) |
| ***B22F 3/24*** | (2006.01) |
| ***B22F 7/00*** | (2006.01) |
| ***B22F 9/04*** | (2006.01) |
| ***C22C 23/06*** | (2006.01) |

(52) U.S. Cl.
CPC ............. *A61L 27/427* (2013.01); *A61L 27/32* (2013.01); *A61L 27/58* (2013.01); *A61L 29/106* (2013.01); *A61L 29/123* (2013.01); *A61L 29/148* (2013.01); *A61L 31/086* (2013.01); *A61L 31/124* (2013.01); *A61L 31/148* (2013.01); *B22F 1/0003* (2013.01); *B22F 3/1055* (2013.01); *B22F 3/16* (2013.01); *B22F 3/24* (2013.01); *B22F 7/008* (2013.01); *B22F 9/04* (2013.01); *C22C 23/06* (2013.01); *A61L 2400/12* (2013.01); *A61L 2420/02* (2013.01); *A61L 2420/06* (2013.01); *A61L 2430/02* (2013.01); *B22F 2003/1051* (2013.01); *B22F 2003/1054* (2013.01); *B22F 2003/242* (2013.01); *B22F 2009/042* (2013.01); *B22F 2009/043* (2013.01); *B22F 2301/058* (2013.01); *B22F 2301/45* (2013.01); *B22F 2302/256* (2013.01); *B22F 2998/10* (2013.01)

(58) Field of Classification Search
None
See application file for complete search history.

(56) References Cited

U.S. PATENT DOCUMENTS

| | | | |
|---|---|---|---|
| 2,771,359 A | 11/1956 | Morana | |
| 4,652,276 A | 3/1987 | Burden | |
| 8,293,031 B2 | 10/2012 | Gerold et al. | |
| 8,771,751 B2 | 7/2014 | Heublein et al. | |
| 2006/0229711 A1 | 10/2006 | Yan et al. | |
| 2008/0103594 A1 | 5/2008 | Loffler et al. | |
| 2009/0081313 A1 | 3/2009 | Aghion et al. | |
| 2010/0137975 A1* | 6/2010 | Wittchow | A61L 31/10 623/1.38 |
| 2010/0331966 A1 | 12/2010 | Borck | |
| 2012/0156477 A1 | 6/2012 | Kurze et al. | |
| 2012/0215301 A1 | 8/2012 | Papirov et al. | |
| 2013/0041455 A1 | 2/2013 | Gerold | |
| 2013/0195714 A1 | 8/2013 | Lyon | |
| 2014/0010699 A1* | 1/2014 | Horstemeyer | C22C 1/0408 419/11 |

FOREIGN PATENT DOCUMENTS

| | | |
|---|---|---|
| DE | 19731021 A1 | 1/1999 |
| EP | 2416812 B1 | 1/2013 |
| WO | 2010119193 A2 | 10/2010 |
| WO | 2010188193 A3 | 10/2010 |

(Continued)

OTHER PUBLICATIONS

Kondoh, K. and T. Luangvaranunt, Materials Transactions 44(12): 2468-2474 (2003).*

(Continued)

*Primary Examiner* — David J Blanchard
*Assistant Examiner* — Daniel F. Coughlin
(74) *Attorney, Agent, or Firm* — MacMillan, Sobanski & Todd, LLC

(57) ABSTRACT

Biodegradable, magnesium alloys and composites, articles produced therefrom, methods of making the same, and methods of using the same are described.

11 Claims, 15 Drawing Sheets
(10 of 15 Drawing Sheet(s) Filed in Color)

(56) References Cited

FOREIGN PATENT DOCUMENTS

| | | | |
|---|---|---|---|
| WO | 2011051424 | A1 | 5/2011 |
| WO | 2011117298 | A1 | 9/2011 |
| WO | 2011117628 | A1 | 9/2011 |
| WO | 2012088112 | A1 | 6/2012 |

OTHER PUBLICATIONS

Angrisani et al., "Rare Earth Metals as Alloying Components in Magnesium Implants for Orthopaedic Applications", Intech, 2012, pp. 1-22.

Chaim et al., "Sintering and densification of nanocrystalline ceramic oxide powders: a review", Advances in Applied Ceramics, 2008, vol. 107, No. 3, pp. 159-169.

Ferro et al., "Magnesium alloys of the rare earth metals: systematics and properties", Metallurgical Science and Technology, 1998, vol. 16, No. 1-2, pp. 25-44.

Gray-Munro et al., "The mechanism of deposition of calcium phosphate coatings from solution onto magnesium alloy AZ31", Journal Biomed. Mater. Res. A., 2009, vol. 90, No. 2, pp. 339-350, Abstract Only.

Hamdy et al., "The Effect of Vanadia Surface Treatment on the Corrosion Inhibition Characteristics of an Advanced Magnesium Elektron 21 alloy in Chloride Media", International Journal of Electrochemical Science, 2012, vol. 7, pp. 7751-7761.

Kondoh et al., "New Process to Fabricate Magnesium Composites Using SiO2 Glass Scraps", Materials Transactions, 2003, vol. 44, No. 12, pp. 2468-2474.

Majumdar et al., "Laser processing of materials", Sadhana, 2003, vol. 28, Parts 3 & 4, pp. 495-562.

Shadanbaz et al., "Calcium phosphate coatings on magnesium alloys for biomedical applications: A review", Acta Biomaterialia, 2012, vol. 8, pp. 20-30.

Suryanarayana et al., "Nanocrystalline materials—Current research and future directions", Hyperfine Interactions, 2000, vol. 130, pp. 5-44.

Wang et al., "In Vitro Corrosion and Cytocompatibility of ZK60 Magnesium Alloy Coated with Hydroxyapatite by a Simple Chemical Conversion Process for Orthopedic Applications", International Journal of Molecular Sciences, 2013, vol. 14, pp. 23614-23628.

Zhang et al., "Controlling the Biodegradation Rate of Magnesium Using Biomimetic Apatite Coating", Journal of Biomedical Materials Research Part B: Applied Biomaterials, 2009, vol. 89B, pp. 408-414.

Zheng et al., "Electron-beam-assisted superplastic shaping of nanoscale amorphous silica", Nature Communications, 2010, vol. 1, No. 24, pp. 1-8.

Zhu et al., "Effects if stearic acid on synthesis of nanocomposite WC-MgO powders by mechanical alloying", J. Mater. Sci., 2010, vol. 45, pp. 1817-1822.

PCT International Search Report and the Written Opinion, Application No. PCT/US2015/029202 filed May 5, 2015, dated Jul. 29, 2015, [53-55994/D2013-63].

* cited by examiner

| Formula | Composition Range (wt %) | Symbol | Lattice Parameter (nm) |
|---|---|---|---|
| $Mg_{24}Y_5$ | 35.6-41.3 | cI58 | a = 1.1251 – 1.1277 |
| $Mg_2Y$ | 65 | hP12 | a = 0.6037<br>c = 0.9752 |
| MgY | 77.4 – 78.8 | cP2 | a = 0.3782 – 0.3810 |

BIODEGRADABLE MAGNESIUM ALLOYS AND COMPOSITES

CROSS-REFERENCE TO RELATED APPLICATIONS

This application is a national stage application filed under 35 U.S.C. § 371 of international application PCT/US2015/029202, filed under the authority of the Patent Cooperation Treaty on May 5, 2015, which claims priority to U.S. Provisional Application Ser. No. 61/988,512, filed under 35 U.S.C. § 111(b) on May 5, 2014, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Many types of alloys are traditionally cast, such as those with applications in the transportation industries. Casting is a process in which a metal or a mixture of metals is heated until it is molten, then poured into a mold and allowed to cool and solidify. The as-produced microstructures of these cast products are generally large and non-uniform. Such microstructures lead to fast degradation and make the alloys unsuitable for biomedical implant applications. It would also be difficult for such implants to conform to regulatory protocols because they do not meet the criteria for GMP protocols for CE/FDA certifications.

In addition, casting frequently gives rise to defects such as segregations, precipitation shrinkage, micro- and macro-porosity, and inhomogeneous grain size and grain distribution during solidification. Such defects, which can sometimes be removed by post-processing methods, adversely affect the properties in at least two ways. First, the mechanical properties suffer due to the presence of defects. Second, inhomogeneous microstructure and the formation of intermetallic particles lead to an inhomogeneous degradation rate within the body. For these reasons, casting produces alloys that generally have defects which are undesirable in biomedical implants.

There is a need in the art for biodegradable magnesium alloys suitable for biomedical implant applications and having improved processability and mechanical properties such as strength, ductility, and strain hardening.

SUMMARY OF THE INVENTION

Provided herein is an alloy comprising magnesium and a rare earth element present at a concentration of up to about 15 wt %, wherein the alloy has a nanocrystalline grain size and contains no intermetallic phases. In certain embodiments, the rare earth element is selected from the group consisting of yttrium (Y), gadolinium (Gd), terbium (Tb), dysprosium (Dy), neodymium (Nd), lanthanum (La), cerium (Ce), praseodymium (Pr), and samarium (Sm). In certain embodiments, the rare earth element consists essentially of yttrium. In particular embodiments, the yttrium is present at a concentration of greater than 10 wt %.

In certain embodiments, the alloy further comprises an additive selected from the group consisting of Ti, Al, Zr, Zn, and Mn. In certain embodiments, the rare earth element is present at a concentration in excess of the equilibrium solid solubility concentration of the rare earth element in magnesium. In certain embodiments, the alloy further comprises a Ca—P coating.

In certain embodiments, the alloy is produced by non-equilibrium processing comprising mechanical alloying. In particular embodiments, the alloy is subjected to fast densification by spark plasma sintering. In particular embodiments, the alloy is subjected to fast densification by microwave sintering. In particular embodiments, the alloy is subjected to fast densification by laster-assisted forming. In particular embodiments, the alloy is subjected to fast densification by electron beam-assisted forming.

Further described is a method of making an alloy, the method comprising the steps of mechanically grinding magnesium and a rare earth metal into alloyed powders, compressing the alloyed powders into objects having a desired shape, and densifying the objects via a fast densification process to produce an alloy, wherein the fast densification process is selected from spark plasma sintering or microwave heating. In certain embodiments, densification lasts for about 5 to 15 minutes. In certain embodiments, the method further comprises the step of machining the alloy into a biomedical implant. In certain embodiments, the mechanical grinding is conducted under Ar. In certain embodiments, the mechanical grinding is conducting with a milling media comprising Zirconia balls at a ball-to-powder ratio of about 20:1. In certain embodiments, the mechanical grinding is conducted with a control agent comprising stearic acid. In certain embodiments, the densification comprises sintering at a temperature of about 450° C. for about 10 minutes. In certain embodiments, the method further comprises coating the alloy with a Ca—P composition. In certain embodiments, the concentration of rare earth metal determines the degradation rate of the alloy. In certain embodiments, the rare earth metal consists essentially of yttrium. Further provided is a product of the method.

Further described is a composite comprising magnesium, and silica present at a concentration up to about 15 wt %. In certain embodiments, the composite further includes a rare earth element present at a concentration up to about 15 wt %. In particular embodiments, the rare earth element is not present in an oxide. In particular embodiments, the rare earth element is selected from the group consisting of yttrium (Y), gadolinium (Gd), terbium (Tb), dysprosium (Dy), neodymium (Nd), lanthanum (La), cerium (Ce), praseodymium (Pr), and samarium (Sm). In particular embodiments, the rare earth element consists essentially of yttrium. In certain embodiments, the composite further comprises an additive selected from the group consisting of Ti, Al, Zr, Zn, and Mn. In certain embodiments, the composite consists essentially of magnesium, yttrium, and silica. In certain embodiments, the composite has a nanocrystalline grain size. In certain embodiments, the composite is produced by non-equilibrium processing comprising mechanical alloying. In particular embodiments, the composite is subjected to fast densification by spark plasma sintering. In particular embodiments, the composite is subjected to fast densification by microwave sintering. In particular embodiments, the composite is subjected to fast densification by laster-assisted forming. In particular embodiments, the composite is subjected to fast densification by electron beam-assisted forming. In certain embodiments, the composite further comprises a Ca—P coating. In particular embodiments, the composite is self-healing.

Further provided is article comprising the composite described herein. In certain embodiments, the article is selected from the group consisting of: orthopedic implants, cochlear implants, surgical staples, aneurism coils, vascular closing devices, plates, screws, intramedullary nails and pins, suture anchors, tacks, rods, anastomosis clips or plugs, dental implants, aortic aneurysm graft devices, atrioventricular shunts, heart valves, bone-fracture healing devices, bone replacement devices, endo-prostheses and prostheses in the area of hard and soft tissues, joint replacement devices, tissue regeneration devices, hemodialysis grafts, indwelling arterial catheters, indwelling venous catheters, needles, vascular stents, tracheal stents, esophageal stents, urethral stents, rectal stents, stent grafts, synthetic vascular grafts, tubes, vascular aneurysm occludes, vascular clips, vascular prosthetic filters, vascular sheaths, venous valves, tubular meshes, catheters, and wires.

Further described is a method of making a composite, the method comprising the steps of mechanically grinding magnesium and nano-silica into powders, compressing the powders into objects having a desired shape, and densifying the objects via a fast densification process to produce a composite, wherein the densification process is selected from spark plasma sintering, microwave heating, laser-assisted forming, and electron beam-assisted forming. In certain embodiments, densification lasts for about 5 to 15 minutes. In certain embodiments, an increased concentration of nano-silica results in a slower degradation rate of the composite. In certain embodiments, the method further comprises coating the composite with a Ca—P composition. In certain embodiments, the powders further include a rare earth metal. In particular embodiments, the rare earth metal consists essentially of yttrium. In certain embodiments, the method further comprises the step of machining the composite into a biomedical implant. In certain embodiments, the mechanical grinding is conducted under Ar. In certain embodiments, the mechanical grinding is conducting with a milling media comprising Zirconia balls at a ball-to-powder ratio of about 20:1. In certain embodiments, the mechanical grinding is conducted with a control agent comprising stearic acid. In certain embodiments, the densification comprises sintering at a temperature of about 450° C. for about 10 minutes. Further provided is a product of the method.

Further described is a method of controlling the degradation rate of an alloy, the method comprising the steps of preparing an alloy from magnesium and rare earth metal powders through a fast densification process, applying a Ca—P composition to the alloy to form a coating, and adjusting the thickness of the coating to control the degradation rate of the alloy. In certain embodiments, the composite is converted into bone-like apartie upon degradation. In certain embodiments, the degradation rate of the composite causes the composite to be converted into bone-like apatite in a time period of from about 6 months to about 18 months.

Further described is a method of controlling the degradation rate of a composite, the method comprising preparing a composite from magnesium and silica powders through a fast densification process, applying a Ca—P composition to the composite to form a coating, and adjusting the thickness of the coating to control the degradation rate of the composite. In certain embodiments, the composite further includes a rare earth element.

Further described is a kit comprising a first container housing magnesium, and a second container housing a source of silica. In certain embodiments, the kit further comprises milling media. In certain embodiments, the kit further comprises a rare earth metal.

Further described is a medical implant comprising an alloy provided herein. Further described is a medical implant comprising a composite provided herein.

BRIEF DESCRIPTION OF THE DRAWING

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 1A-1B: Phase diagram of the Mg—Y system (FIG. 1A) and structural properties of the intermetallics in the Mg—Y phase diagram (FIG. 1B).

FIG. 8: X-ray diffraction characterization of the Mg—$SiO_2$ system.

FIG. 9: SEM image of Mg—$SiO_2$ surface after 90 minutes of incubation in simulated body fluid at room temperature.

DETAILED DESCRIPTION OF THE INVENTION

Figure 1A:
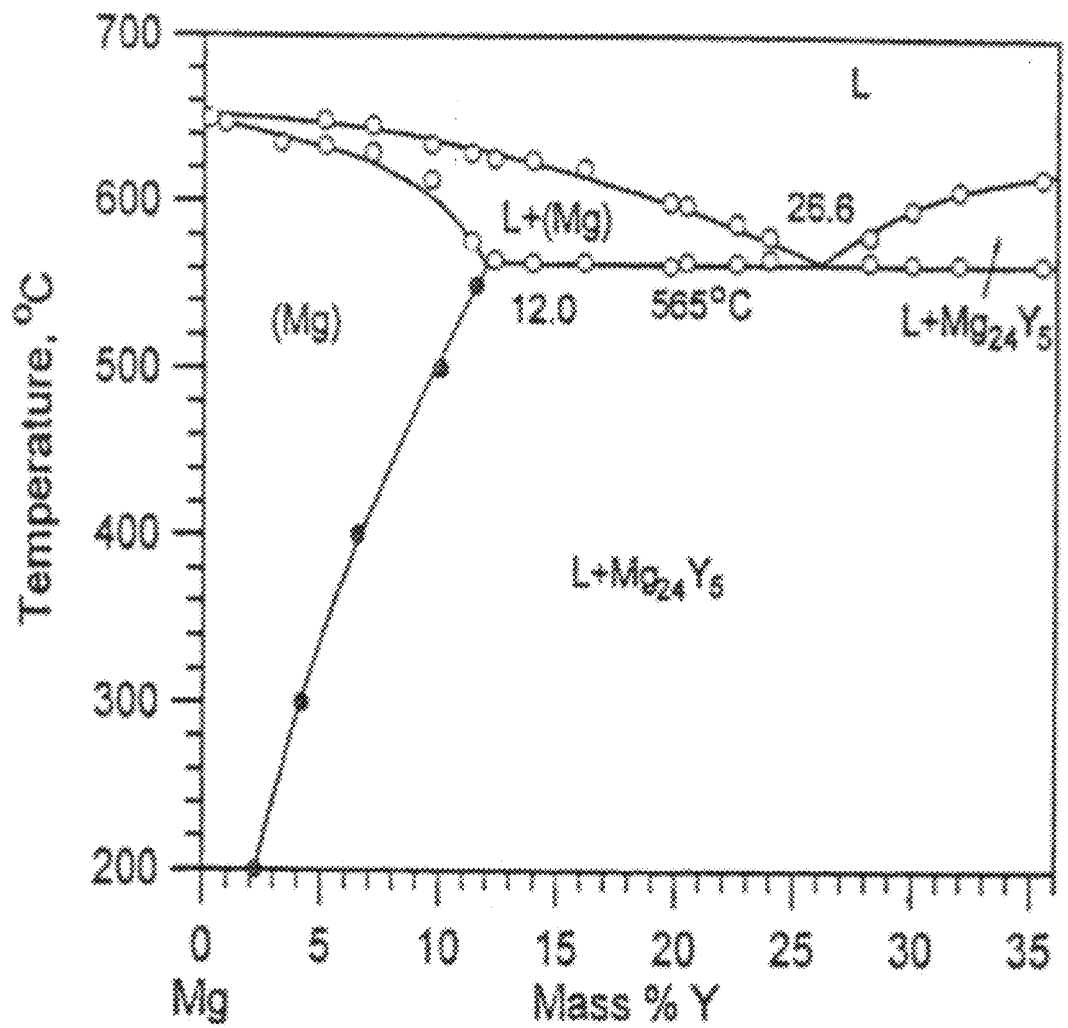
Figure 2A:
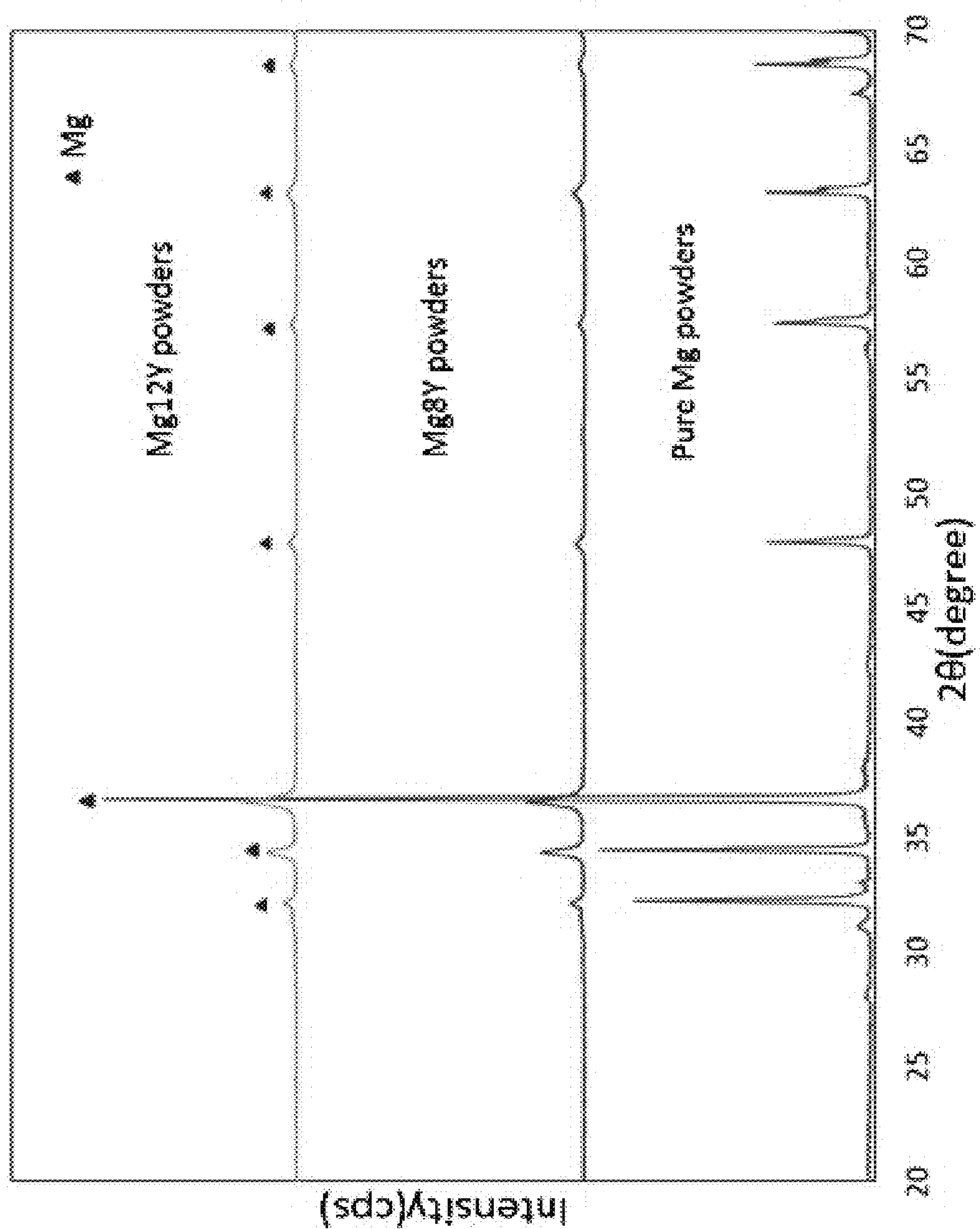
FIGS. 2A-2B: XRD pattern (FIG. 2A) and images (FIG. 2B) of as-synthesized Mg—Y powders.
Figure 2B:
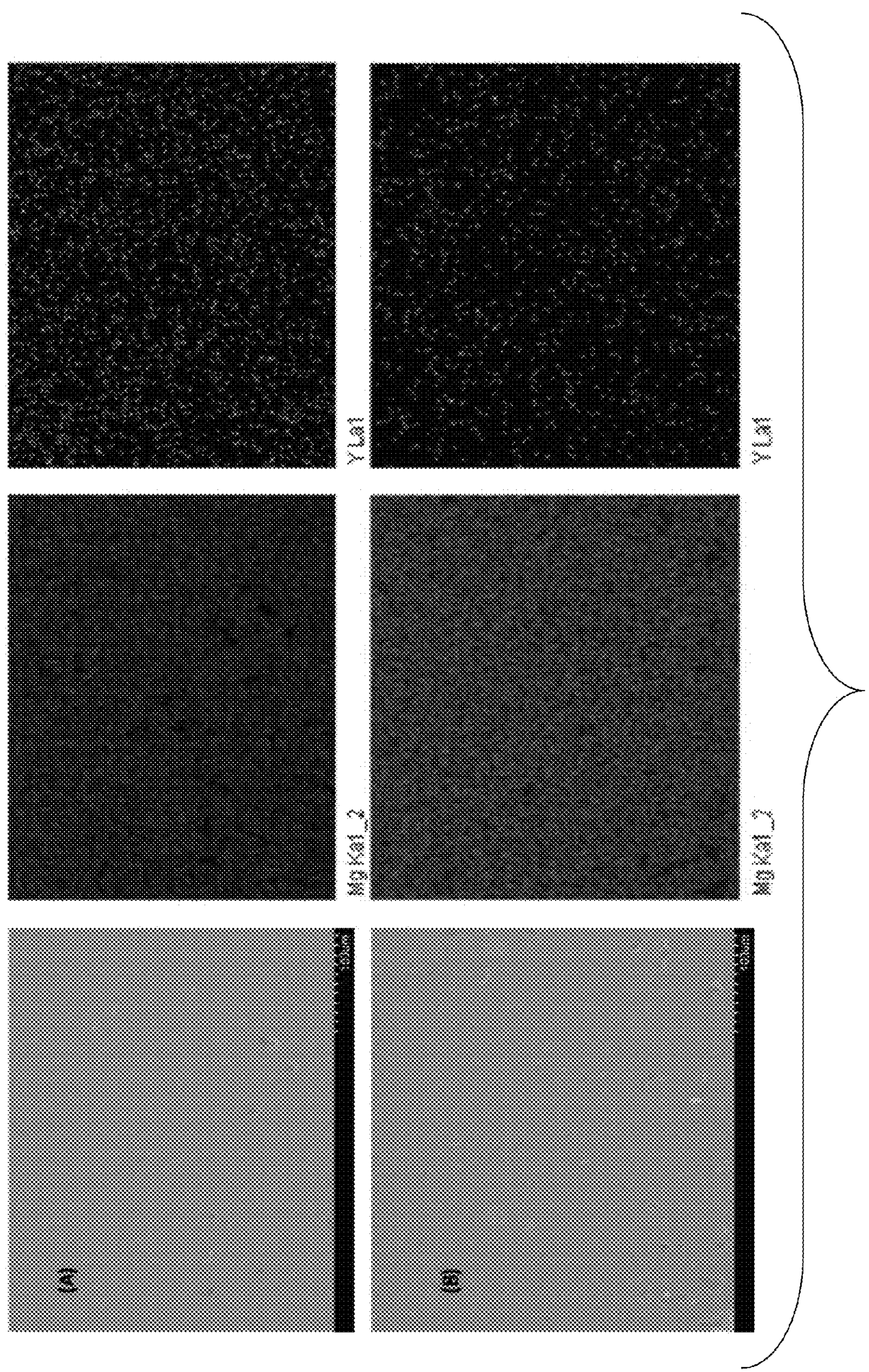
Figure 3:
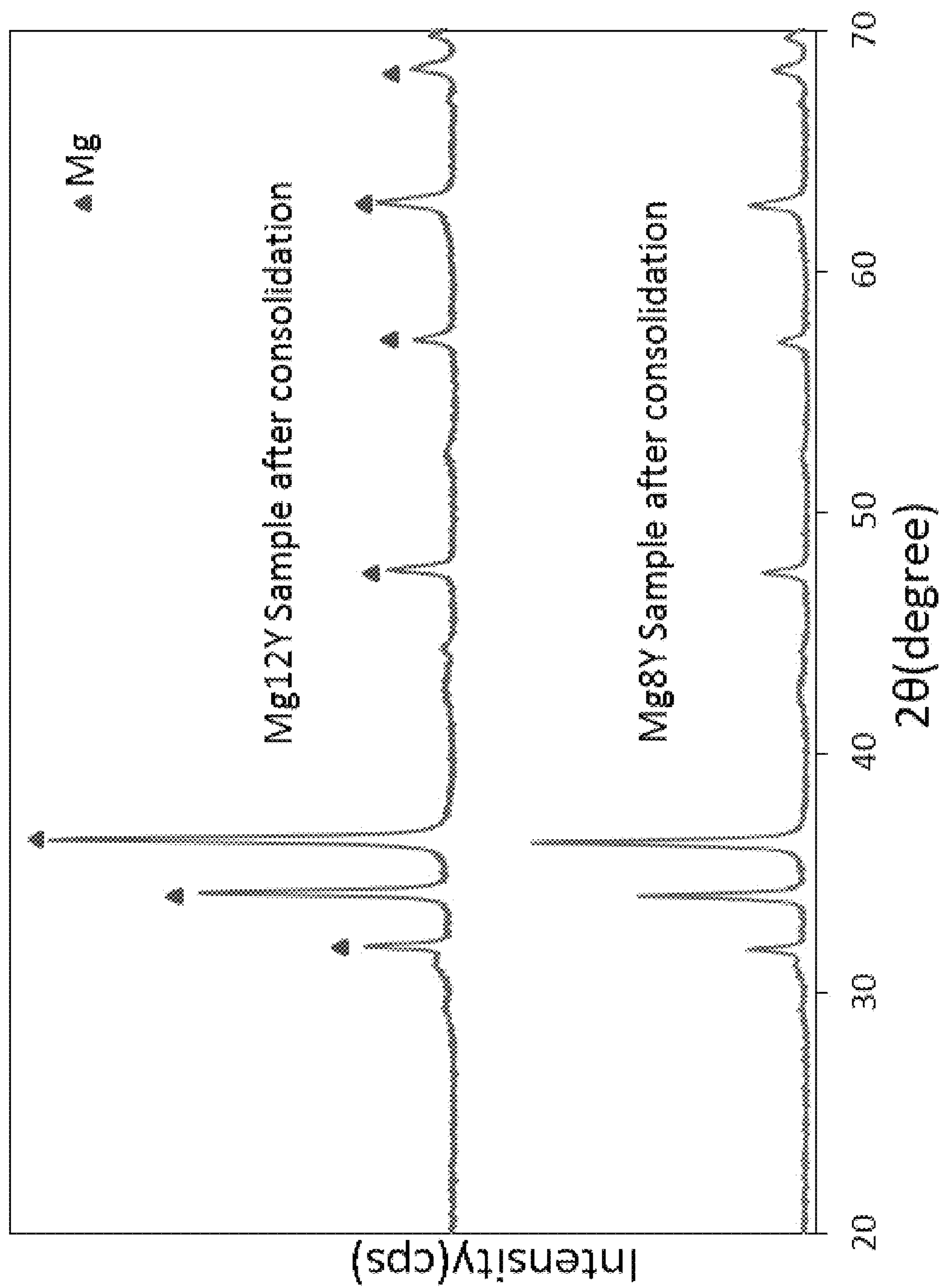
FIG. 3: XRD pattern of Mg—Y alloy after densification.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Definitions

The term "alloy" as used herein refers to a solid solution of a metal and another element. The elements present in an alloy can substitute randomly for one another in the crystal structure.

The term "intermetallic" as used herein refers to a metallic phase containing more than one element, where the different elements are ordered into different sites in the crystal structure and have distinct local environments.

The term "grain" refers to an individual particle in an alloy or polycrystalline material, which may or may not contain twinned regions and subgrains, and in which the atoms are arranged in an orderly pattern.

The term "self-healing" as used herein refers to the ability of a material to repair damage caused by mechanical stress or usage without external stimuli like heat, solvents, or plasticizers.

The phrase "consisting essentially of" means that the composition or method may include additional ingredients and/or steps, but only if the additional ingredients and/or steps do not materially alter the basic characteristics of the composition or method.

General Description

Calcium is a substantial constituent of bone mineral. Like calcium, magnesium is an important element that the human body needs. In fact, magnesium is the fourth-most important cation in the human body, with half of it stored in bone. Thus, the presence of magnesium is well-tolerated in the body, and magnesium-based alloys can be used both in vitro and in vivo. Unlike titanium alloys, magnesium alloys are biodegradable; magnesium degrades in physiological environments to yield magnesium hydroxide and hydrogen, through a process referred to as corrosion. Magnesium alloys are also stronger than biodegradable calcium phosphate ceramics and biopolymers. Furthermore, magnesium alloys have a lower Young's modulus, meaning implants fabricated from them cause less stress shielding.

Magnesium alloys can generally be divided into three major groups: pure magnesium with traces of other elements, aluminum-containing alloys, and alloys that are aluminum-free. Conventional ASTM nomenclature is used for alloy designation. Typical Al-containing magnesium alloys include AZ91, AZ31, AE21, and the like. Some alloys consist of magnesium, aluminum, and rare earth elements (REs). However, many utilized rare earth-containing alloys, such as WE43, are aluminum-free. The composition WE43 contains a predominant addition of zirconium and other REs. REs are generally added in the form of mischmetal, comprising many different REs. Introducing REs into magnesium via mischmetal is not only cheap, but the presence of various REs with varying degrees of solubility may also create some strength enhancement. In the automotive industry, mischmetal typically has about 50% cerium, 45% lanthanum, and small amounts of neodymium, praseodymium, or yttrium. Cost is generally a priority for these alloys. However, stopping the degradation of these alloys is a challenge. RE-containing magnesium alloys have lower degradation kinetics than conventional alloys. Furthermore, alloys for biomedical applications have different standards. The regulatory requirements of good laboratory practice and good manufacturing practice for biomedical applications call for stringent composition of alloys, meaning mischmetal does not suffice. In addition, alloys produced by the casting route tend to have large inhomogeneous grain structure, which results in non-uniform and fast degradation, preventing the alloys from being used for implant applications.

Provided herein are magnesium alloys useful for, inter alia, biomedical implants in orthopedic, dental, or cardiovascular applications. The alloys of the present disclosure generally comprise magnesium and a rare earth element, where the rare earth element is present at a concentration up to about 15 wt %. In particular embodiments, the rare earth element is present in the composition at a concentration greater than about 10 wt %. Unlike cast alloys, which generally have lessened compositional and microstructural homogeneity, a coarse microstructure, and a decreased ability to incorporate additional amounts of rare earth elements, the alloys of the present disclosure are produced in nanocrystalline grain size and contain no intermetallic phases. The alloys are biodegradable, rare earth-containing magnesium alloys made through a powder processing method. These alloys are significantly stronger than biodegradable calcium phosphate ceramics or biopolymers. The powder metallurgical techniques used to create the alloys slow down their degradation rate and enhance their initial strength. The alloys are particularly useful for biomedical implants, though they can be machined or fabricated into a wide variety of articles.

In general, the phase diagrams of rare earths and magnesium can be divided into two groups. The first group contains elements with large solid solubilities in Mg, such as yttrium (Y), gadolinium (Gd), terbium (Tb), or dysprosium (Dy). The second group contains elements showing only limiting solubility in Mg, such as neodymium (Nd), lanthanum (La), cerium (Ce), praseodymium (Pr), or samarium (Sm). FIGS. 1A-1B show the phase diagram of the Mg—Y system, along with the mechanical properties of the intermetallic phases in this system. As per the phase diagram, the maximum solid solubility of Y into the Mg lattice is about 11.5 wt %. In certain embodiments, the rare earth element in the presently described alloys is yttrium, which is especially advantageous because of the similarity of standard electrochemical potentials between Y and Mg (−2.372 V). Having a similar standard electrochemical potential improves the corrosion resistance and helps control the degradability of the alloy. In certain embodiments, the rare earth element is gadolinium. The presence of gadolinium is important in providing contrast in imaging techniques such as MRI.

Of all REs, yttrium is the most effective strengthener because of its high solubility and the large size difference between the host and the solute. A further gain in strength occurs by adding greater amounts of Y to the Mg host. However, with a greater addition of yttrium, the solubility limit is reached, thus precipitating $Mg_{24}Y_5$ intermetallic. Precipitation of the $Mg_{24}Y_5$ intermetallic reduces the ductility and results in inhomogeneous degradation. Therefore, extending the solid solubility of Y into the Mg lattice while forming nanostructured alloys to improve Y content in Mg alloys is desirable. In any event, other REs can be applied to Mg for strengthening, and the present disclosure is by no means limited to yttrium-magnesium alloys. The alloys can be made from solid solutions of magnesium and any of the 17 rare earths: scandium, yttrium, lanthanum, cerium, praseodymium, neodymium, promethium, samarium, europium, gadolinium, terbium, dysprosium, holmium, erbium, thulium, ytterbium, and lutetium.

The biodegradable Mg alloys have a nanocrystalline grain structure, and improved strength from the synergistic application of solid solution and grain size strengthening mechanisms. The addition of yttrium up to 2 wt % in a single-phase Mg—Y alloy increases strength; without wishing to be bound by theory, it is believed that greater addition of yttrium increases strength even more. Strength also improves with $(D)^{-1/2}$, where D is the grain size. Therefore, decreasing the grain size to about 100 nm increases strength levels further. Decreasing the grain size also improves corrosion resistance.

RE-Mg alloys have been made through non-equilibrium rapid solidification techniques such as chill block melt spinning, splat cooling, and magnetron sputtering. However, rapid solidification processes involving bulk melting need a greater deal of care and expertise because of the wide difference in the melting points of Mg and REs. A powder metallurgical process such as mechanical alloying, on the other hand, is eminently suitable for non-equilibrium processing to elicit the same benefits without having the constituents undergo bulk melting. The alloys herein are produced from a method that involves the mechanical alloying of powders, followed by the fast densification through an accelerated sintering route such as microwave sintering, spark plasma sintering, plasma spraying, or electron/laser-beam assisted processes. Because the alloys can have constituents with a substantial difference in their melting points (for instance, Mg and Y have melting points of 650° C. and 1520° C., respectively), the powder route utilized herein is an improvement over casting. Also, the biocompatibility of the resulting alloy is enhanced by avoiding toxic components (such as zinc or aluminum) in the alloy or the corrosion products.

Mechanical alloying has all the attributes of non-equilibrium processes (meaning more solutes can be dissolved), but without the requirement of bulk melting of the constituents. Mechanical alloying has many benefits, such as, but not limited to: allowing for alloy formation from constituents with a wide difference in melting points, the extension of solid solubility, the refinement of grain size down to nanometers, amorphization, the triggering of exothermic or displacement reactions, the production of complex shapes with high tolerance, and the possibility for scaling up.

In the mechanical alloying process, the particles undergo vigorous grinding and shaking in contact with the grinding media. This process results in welding and fracture, which trigger diffusion of atoms along or across grain boundaries. As a result, alloy formation takes place. For implant applications, the extension of solid solubility is generally preferable as compared to the formation of intermetallics. The presence of intermetallics sets up local galvanic cells, resulting in inhomogeneous biodegradation kinetics. In accordance with the present disclosure, the incorporation of more solute (such as yttrium) enhances strength via solid solution strengthening, provided the powders are consolidated by means of an activated sintering process. Likewise, nanocrystalline grains can participate in the grain boundary strengthening process.

The alloys of the present disclosure are made by mechanical alloying to synthesize the alloy powders by vigorously grinding the constituents (such as Mg and Y), followed by fast sintering techniques such as microwave sintering or spark plasma sintering in order to densify the mechanically alloyed powders to about 95% of theoretical density in about five to ten minutes. This fast processing yields nanocrystalline grain size with uniform nanostructure having improved mechanical properties.

Mechanical alloying is used to produce powder compositions containing known amounts of REs. In certain embodiments, the RE is present at a concentration ranging from 0 to about 15 wt %. In the process, no intermetallic phases such as $Mg_{24}RE_5$, $Mg_2RE$, or MgRE are formed, thereby increasing strength. Optionally, nano-silica can be added to enhance the bioactivity and form a nano-composite. The addition of silica results in intermetallic formation and increases the formation of phosphate coatings, which makes intermetallic formation tolerable. External parameters such as mill type, intensity of milling, atmosphere, ball-to-powder ratio, milling time, temperature, and the type and nature of process control agent can affect the characteristics of powders. A typical milling time is about 10 hours, but other milling times are entirely within the scope of the present disclosure. The as-prepared Mg-RE powders can be densified into a net-shape using an accelerated high temperature process such as, but not limited to, microwave sintering, spark plasma sintering, laser-assisted sintering, and electron beam-assisted sintering. In certain embodiments, the resulting composition is a stoichiometric Mg-RE compound with a very homogeneous nanostructure.

Prior to densification, the alloyed powders can be formed or machined into any desired shape, including complex shapes. For example, the powders can be compressed into pellets, and the pellets can be machined into a product mold. Compression can be done through, for example, hydraulically-operated machining or extrusion molding.

In accordance with the present disclosure, the mechanically alloyed powders undergo subsequent densification by the application of temperature, pressure, and/or current. In one method, fast sintering through activated microwave sintering is used due to the fact that certain minerals and ceramics absorb microwaves and become self-heated. In this manner, heating is generated within the alloyed powders. Metals, on the other hand, reflect microwaves sometimes. Due to the peculiar generation of heat in situ rather than radiative heat transfer from the furnace heating element, the core of the powder compact is dense while surface heat loss creates surface porosity, a feature desirable in implants for osseointegration. Without wishing to be bound by theory, it is believed this is also the reason why very fast heating rates can be obtained.

Alternatively, spark plasma sintering can be used and also result in very fast densification. Application of very high current density through the powder compact creates localized plasma between the powder particles, leading to fast densification kinetics. In this manner, the mechanically alloyed powders are consolidated by the simultaneous application of pressure, temperature, and electric current. A very high temperature can be generated within a short time frame using spark plasma sintering. Close to full density can be achieved within 10-15 minutes. Spark plasma sintering can maintain the nanocrystalline structure of the alloys, as well as the non-equilibrium characteristics.

In other methods, additive manufacturing techniques using laser- and electron beam-assisted techniques also produce dense compacts of complex shapes within a short timeframe. All the aforementioned processes can result in fast densification while retaining the non-equilibrium features of powders.

The addition of silica into the composition, which results in intermetallic formation and an increase in the formation of phosphate coatings, significantly reduces the magnesium degradation rate. Thus, provided herein are composites containing magnesium and silica, the composites generally being suitable for biomedical implant applications. The silica is generally present in the composites at a concentration ranging from zero to about 15% by weight. In some cases, the composites further include a rare earth metal up to about 15% by weight. Amorphous nano-silica, a colloidal system, is fabricated into the magnesium alloys without damaging magnesium strength. This incorporation makes the magensium alloys highly bioactive, giving them the ability to form a bone-apatite coating on the surface as a protective layer to corrosion. In certain embodiments, the silica is not amorphous, thereby enhancing bioactivity and further slowing the degradation. The addition of nano-silica can also improve mechanical strength and bioactivity. Bioactivity in this context refers to the ability of implant materials to form strong bone-bonding to tissues, thus improving fixation and stability of the implant in vivo. The nano-silica intensifies apatite (similar to bone mineral composition) coating formation on the Mg (or Mg-RE) surface, thereby improving implant life in vivo. Nano-silica also stimulates cell proliferation due to the positive impact of the presence of $Si^{2+}$ ions on cell activity.

Figure 6:
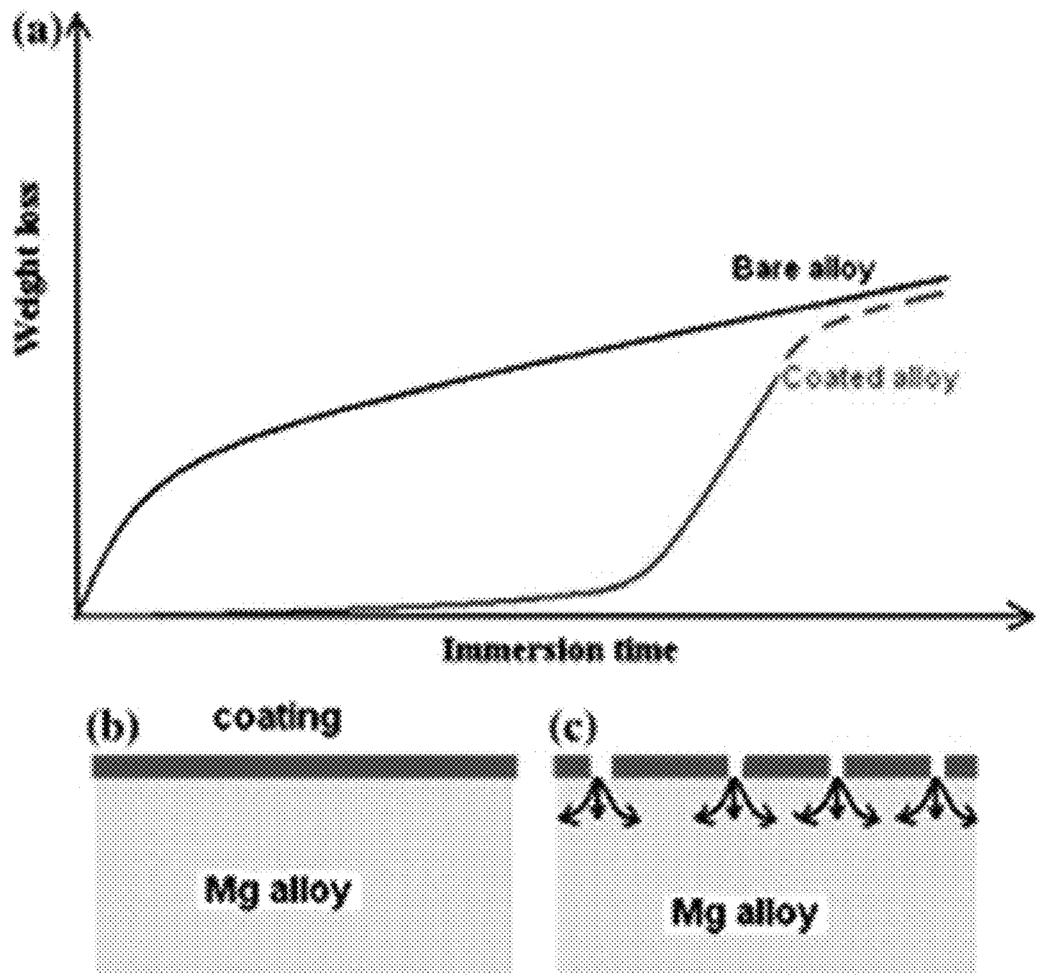
FIG. 6: Graph and illustrations demonstrating the effect of a coating layer on the surface of a Mg alloy. Once the coating is damaged, magnesium degradation can be significantly accelerated.
Figure 7:
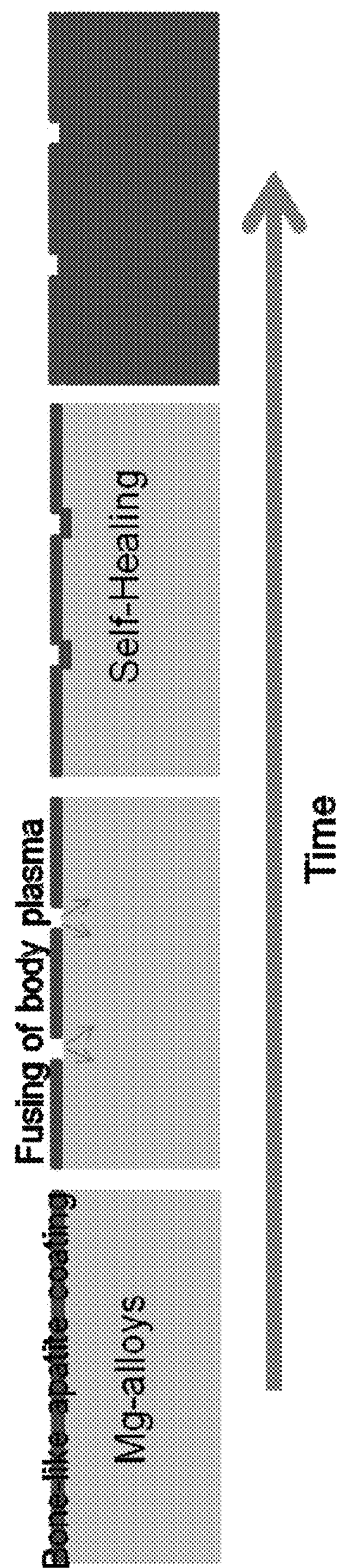
FIG. 7: Illustration of the self-healing process of the Mg-silica system.

The corrosion resistance of the alloys and composites described herein can be enhanced to slow degradation and accelerate the formation of a protective layer. The degradation of the alloys or composites can be further controlled by the fabrication of a coating layer on the surface of the alloy or composite. By way of a non-limiting example, the coating can be a Ca—P composition. Suitable Ca—P compositions include compounds within the CaO—$P_2O_5$ (Ca—P) binary system, such as, but not limited to: hydroxyapatite ($Ca_{10}(PO_4)_6(OH)_2$), tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), and octacalcium phosphate (OCP, $Ca_8H_2(PO_4)_6.5H_2O$). Once the coating is damaged, the magnesium degradation can be significantly accelerated. This effect is illustrated in FIG. 6. When silica is present in the composition used as an implant, there is a built-in coating of Ca(Mg)—P on the surface of the implant, even when scratched. As illustrated in FIG. 7, the Mg-silica system is a self-healing system; once the outer coating layer is damaged, the fused solution can react with inner Mg to form a new coating structure in less than 2 hours. This coating is a bone-like apatite that is a degradable Ca—P material with a much slower degradation rate. Eventually, generally after about 6-18 months, the whole implanted composition is converted into bone-like apatite.

Through the methods described herein, a biodegradable implant can be degraded over time at a known, pre-designed degradation rate that could, for example, support a bone until the completion of the healing process. This alleviates the need to perform an unnecessary surgical procedure to remove the supporting implant, which significantly reduces the costs and risks involved. The desired time is typically determined according to factors such as, but not limited to, the nature of the impairment, the site of implantation, and the characteristics (e.g., age, weight, height) of the individual being treated. By way of a non-limiting example, the degradation rate of an alloy or composite described herein can be tuned by the concentration of the rare earth element. As other examples, the degradation rate can be slowed by adding silica or by increasing the thickness of a Ca—P coating on the surface of the alloy or composite. Furthermore, so as to reliably control the degradation rate, the use of non-biocompatible elements in the alloys or composites can be avoided. These elements include lead, beryllium, copper, thorium, aluminum, zinc, and nickel.

The densified alloys and composites described herein can be further processed by methods such as extrusion, rolling, forging, drawing, laser cutting, or other mechanical working into various configurations, shapes, and/or dimensions. As one non-limiting example, an alloy or composite can be pressed into a close cavity so as to deform the alloy or composite into the shape of the cavity. This type of forging treatment is especially useful for the preparation of screws and/or plates. In certain embodiments, forging is conducted at a temperature in the range of from about 300° C. to about 450° C., and at a pressure ranging from about 2 times to about 5 times higher than the pressure indicated for extrusion treatments.

The machined and/or processed alloy or composite can optionally be subjected to a surface treatment or polishing by mechanical and/or chemical means. Surface treatments may be aimed at modulating the corrosion rate and/or biocompatibility of the alloy. Suitable techniques for this purpose include, but are not limited to, conversion coating and anodizing (which is an electrolytic process used for producing an oxide film on metals and alloys as a passivation treatment, and is typically effected by applying a DC or AC current). Additionally, the articles can be passivated via passivation techniques such as immersion in an alkaline solution or immersion in an organic solution.

The corrosion rate of the alloys and composites described herein, or the articles made therefrom, can be tested and determined according to international standards. For example, ASTM G15-93 delineates standard terminology relating to corrosion and corrosion testing. ASTM G5-94 provides guidelines for making potentiostatic and potentiodynamic anodic polarization measurements. ASTM G3-89 delineates conventions applicable to electrochemical measurements in corrosion testing. ASTM G31-72 is a standard practice for laboratory corrosion testing of animals.

Any of the alloys or composites descried herein, or articles produced therefrom, can be utilized for a wide variety of biomedical applications. Suitable biomedical applications include, but are not limited to: orthopedic implants, cochlear implants, surgical staples, aneurism coils, vascular closing devices, plates, screws, intramedullary nails and pins, suture anchors, tacks, rods, anastomosis clips or plugs, dental implants, aortic aneurysm graft devices, atrioventricular shunts, heart valves, bone-fracture healing devices, bone replacement devices, endo-prostheses and prostheses in the area of hard and soft tissues, joint replacement devices, tissue regeneration devices, hemodialysis grafts, indwelling arterial catheters, indwelling venous catheters, needles, vascular stents, tracheal stents, esophageal stents, urethral stents, rectal stents, stent grafts, synthetic vascular grafts, tubes, vascular aneurysm occludes, vascular clips, vascular prosthetic filters, vascular sheaths, venous valves, tubular meshes, catheters, and wires. The alloys and composites are especially useful for biomedical implants, which are devices introduced into the human body via a surgical method that can include screws, plates, nails, surgical suture material, intestinal clamps, vascular clips, prostheses, and anchoring elements. Naturally, the degradation rate of the alloy or composite can be designed based on the desired application. For instance, biodegradable stents are typically designed to disintegrate within about 3-6 months, whereas alloys or composites used for orthopedic implants should generally last for longer, such as about 1.5 years, so as to allow sufficient bone formation at the impaired site.

The alloys or composites can also be in the form of a coating over all, or a portion, of an external surface of an article, such as an implant. By way of a non-limiting example, a rapid solidification process such as vapor sputtering can be used to apply a surface coating on top of a biodegradable or non-biodegradable material. Such a coating can delay the corrosion of the underlying implant material for a desired period of time. Similarly, a coating such as a magnesium carbonate coating can be applied to the alloys or composites so as to further inhibit corrosion. A magnesium carbonate coating can be applied to the surface of the alloy or composite by exposing at least part of the surface of the alloy or composite to an atmosphere comprising humid carbon dioxide.

The alloys and composites described herein can also be utilized for forming multi-layered articles, in which two or more layers are constructed as, for example, a core/coat structure. An article can be a double-layered article composed of a core layer and a coat layer applied thereon, or alternatively, two or more coat layers, each being applied on a different portion of the core layer. The article can alternatively be a multi-layered article composed of a core layer and two or more coat layers sequentially applied on the core layer. By way of non-limiting examples, the coat layer(s) can comprise a porous composition such as, but not limited to, polyimides, hydroxyapatite, gelatin, polyacrylates, polyglycolic acids, polylactides, and the like. Such coatings can be applied by various methodologies and can be used to confer biocompatibility to the article and/or regulate the corrosion degradation kinetics of the articles.

Because the alloys and composites described herein can be porous, it is possible to incorporate various substances which provide the alloys or composites with added benefits within the pores. Such substances include, but are not limited to, biologically active substances and agents that provide the alloy or composite with improved biocompatibility, degradation kinetics, and/or mechanical properties. Any of the articles fabricated from the alloys or composites described herein can have one or more active substances attached to the surface of the alloy or composite, or encapsulated within pores of the alloy or composite. Suitable active substances include molecules, compounds, complexes, adducts, and/or composites that exert one or more beneficial activities such as therapeutic activity, diagnostic activity, biocompatibility, corrosion kinetic regulation, hydrophobicity, hydrophilicity, surface modification, or aesthetic properties. Active substances that exert therapeutic activity include, but are not limited to, genetic therapeutic agents, non-genetic therapeutic agents, growth factors, bone morphogenic proteins, osteoprogenitor cells, angiogenesis promoters, cytokines, chemokines, chemo-attractants, chemo-repellants, drugs, proteins, agnoists, amino acids, antagonists, anti-histamines, antibiotics, antibodies, antigens, antidepressants, immunosuppressants, anti-hypertensive agents, anti-inflammatory agents, antioxidants, antiproliferative agents, antisenses, anti-viral agents, chemotherapeutic agents, anti-viral agents, fatty acids, haptens, hormones, inhibitors, ligands, DNA, RNA, oligonucleotides, nucleic acid constructs, peptides, polypeptides, enzymes, saccharides, polysaccharides, radio-isotopes, radiopharmaceuticals, steroids, toxins, vitamins, viruses, stem cells, and any combination thereof.

EXAMPLES

Two alloy compositions were prepared: the first having 8 wt % of Y in Mg, and the second having 12 wt % of Y in Mg. Elemental Mg (~60 mesh of 99% purity) and Y (~69 mesh of 99% purity) were milled using a SPEX mill (Model 8000), located inside a glove box flushed with ultra-pure Ar. All the powder handling took place within the glove box. The SPEX mill was chosen because of its high efficiency. Zirconia balls were used as the milling media, and hardened steel vials were filled with these balls at the ball-to-powder ratio of 20:1, which is a higher ratio than conventionally used. This ratio can be increased upwards to increase the intensity of mixing. Care was taken not to fill more than half of the available volume. Since the powders are on the coarser side, individual powders required milling separately before mixing them together. Though a process control agent such as stearic acid can be useful in a mechanical alloying process, no process control agent was used in this example. A milling time of 10 hours was used to to synthesize the powders in order to minimize contamination.

After mechanical alloying, the powders were spark plasma sintered using a modified uniaxial hot press using graphite die and plunger lined with graphite foil. The process was performed under vacuum. The powders were compacted with 60 MPa, applying a current through the graphite die. The sintering temperature was 450° C., and the sintering lasted for 10 minutes. The preliminary experiments were all able to achieve at least 97% of the theoretical density while retaining the nanocrystalline grain size without the formation of any intermetallics.

In another process, the powders were alternatively compacted to fabricate pellets. Initial uniaxial pressing was conducted within the glove box. The pellets could be cold isostatically pressed (CIPed) in a press with a maximizing pressure capability of 60 ksi. The compacted pellets were surrounded by SiC susceptors to couple microwaves effectively. The final densification of the samples took place in a semi-industrial microwave furnace (Microwave Materials Technology, Knoxville, Tenn.). The system has a variable-power output magnetron source capable of operating from 0 to 3 kW at 2.45 gHz. Some of the sintering experiments resulted in a density value of 97% of the theoretical density with a surface porosity layer, which is useful for cell attachment.

The protocols described in this example were used to produce Mg—$SiO_2$ compositions as well. Table 1 shows the mechanical properties (namely, relative density and nominal hardness values) of these compositions compared to a Mg control.

TABLE 1

Mechanical properties of spark plasma sintering densified Mg—Y alloy, Mg—$SiO_2$ compound, and control Mg

| | Relative density | $HV_{0.5}$ |
|---|---|---|
| Alloy (wt. %) | | |
| Mg—0Y | 100% | 40 |
| Mg—8Y | 98.2% | 102 |
| Mg—12Y | 97.3% | 85 |
| Composite (wt. %) | | |
| Mg—0$SiO_2$ | 100% | 40 |
| Mg—5$SiO_2$ | 99% | 91 |
| Mg—10$SiO_2$ | 99% | 112 |
| Mg—15$SiO_2$ | 99% | 126 |

Figure 4A:
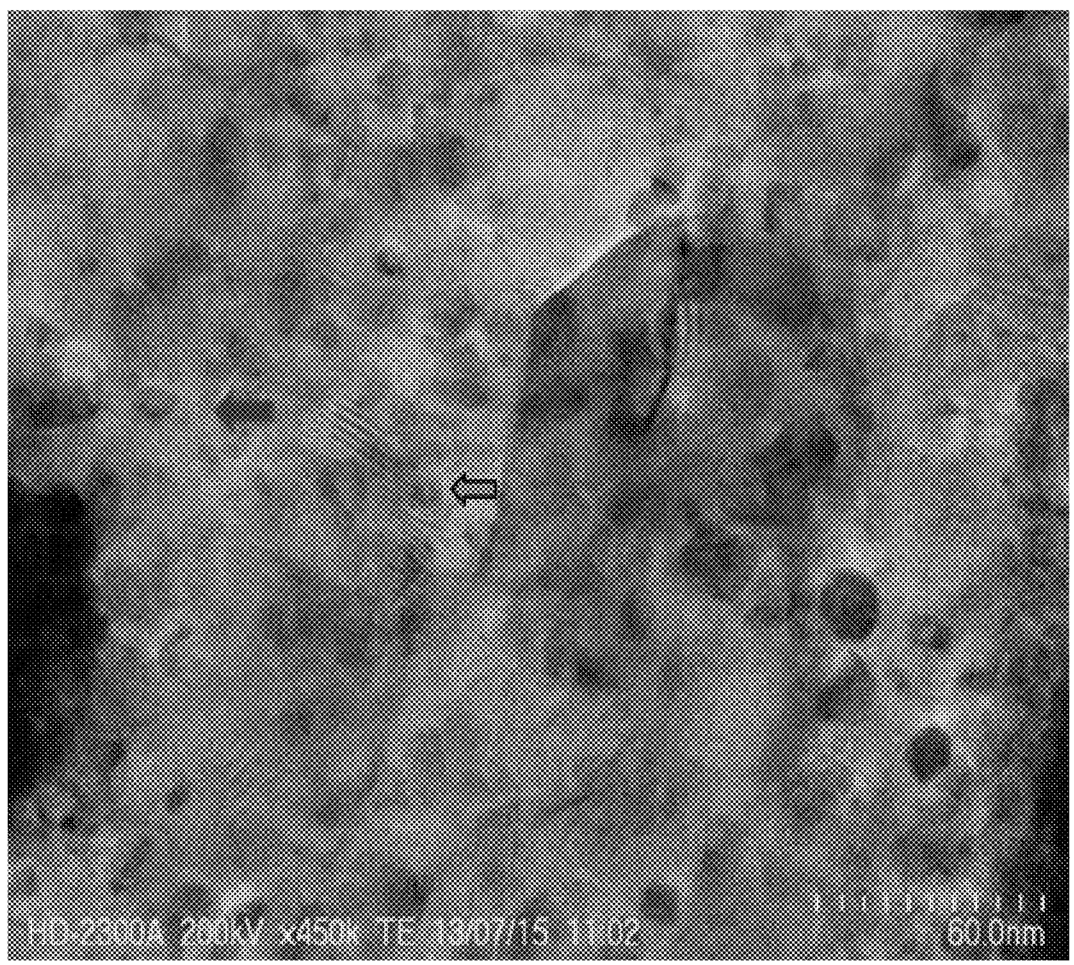
FIGS. 4A-4B: TEM images of Mg—Y alloy (FIG. 4A) and Mg—$SiO_2$ composite (FIG. 4B) densified by spark plasma sintering. The colored arrows in FIG. 4A show the formation of nanocrystals, containing fringe patterns of planes under the specific imaging conditions utilized. Other nanocrystals would become prominent under other imaging conditions.
Figure 4B:
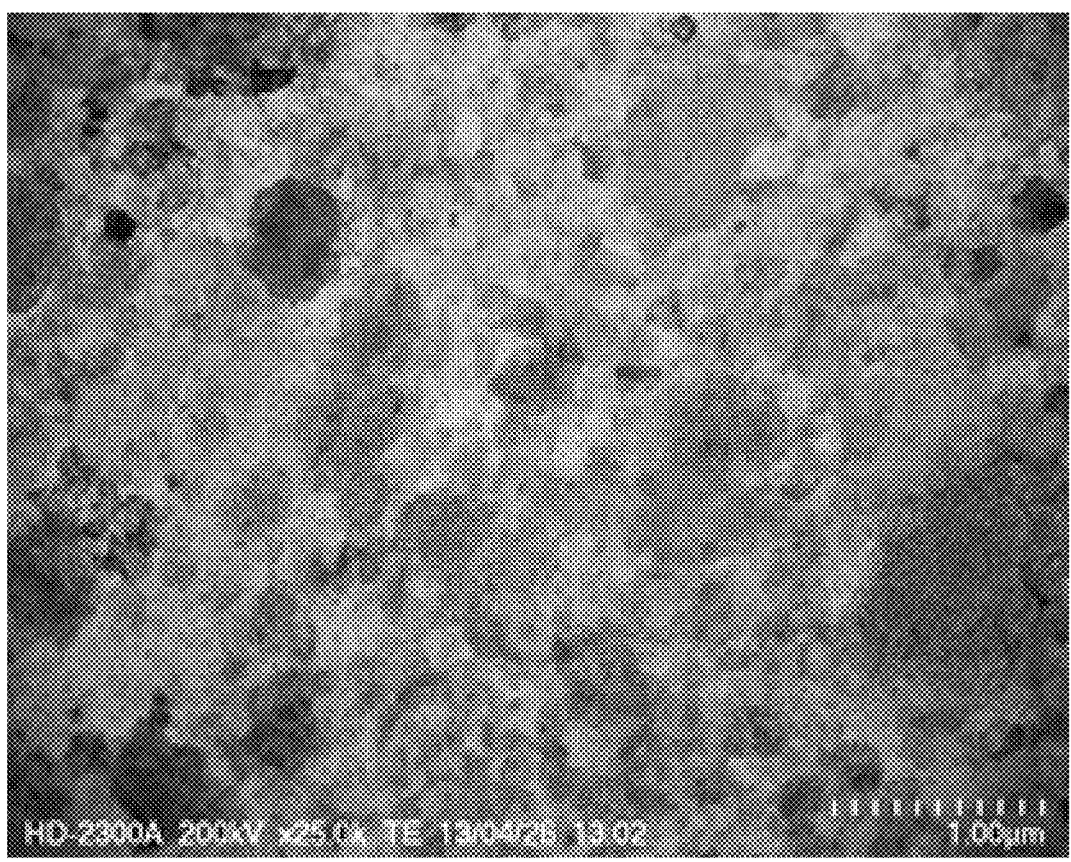
Figure 5A:
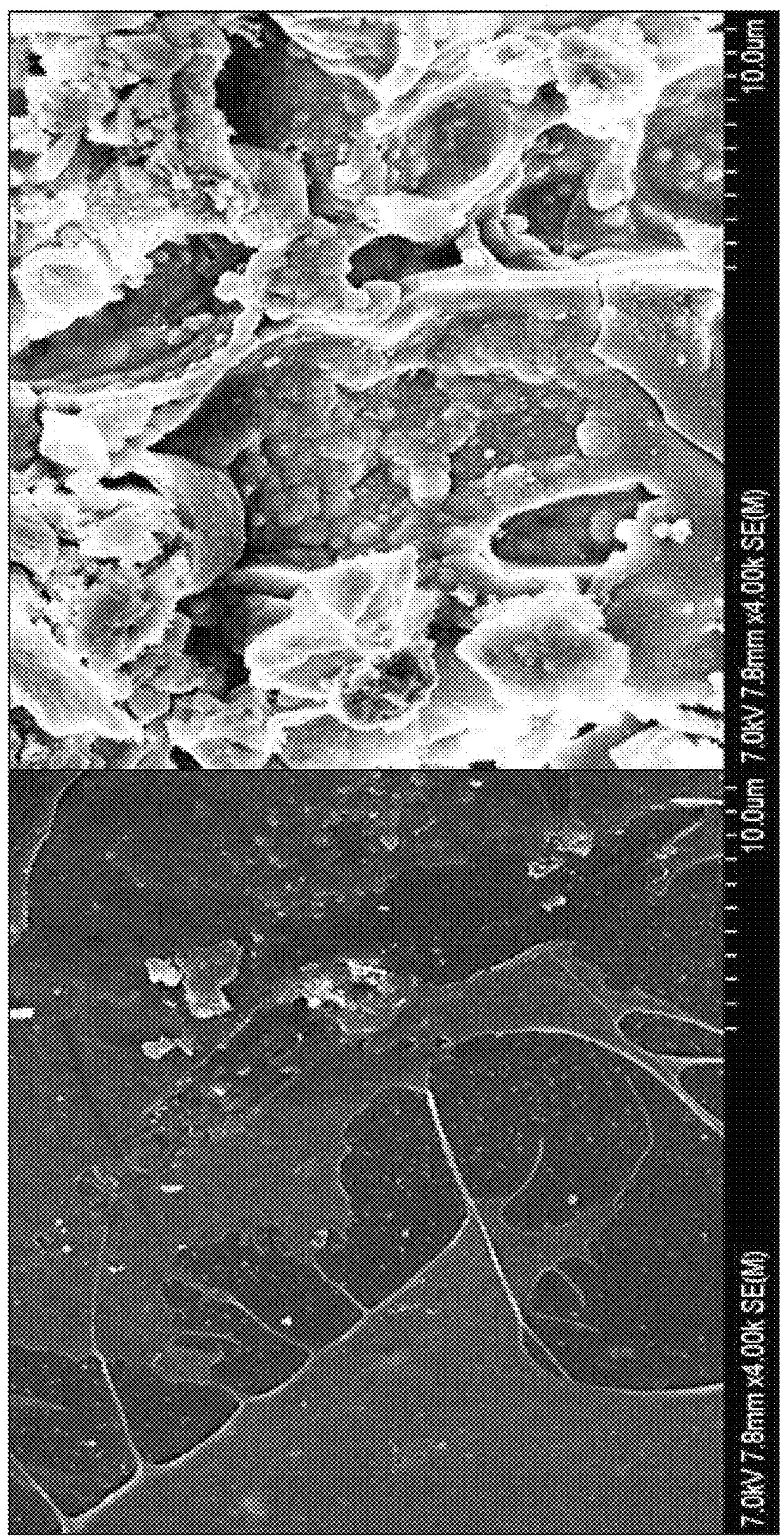
FIGS. 5A-5B: SEM images of a Mg—Y alloy (FIG. 5A) and chart showing cell numbers present on a Mg—Y alloy, with Y present at a concentration of 8 wt %, compared to a Mg-PLA control, after four days (FIG. 5B).
Figure 5B:
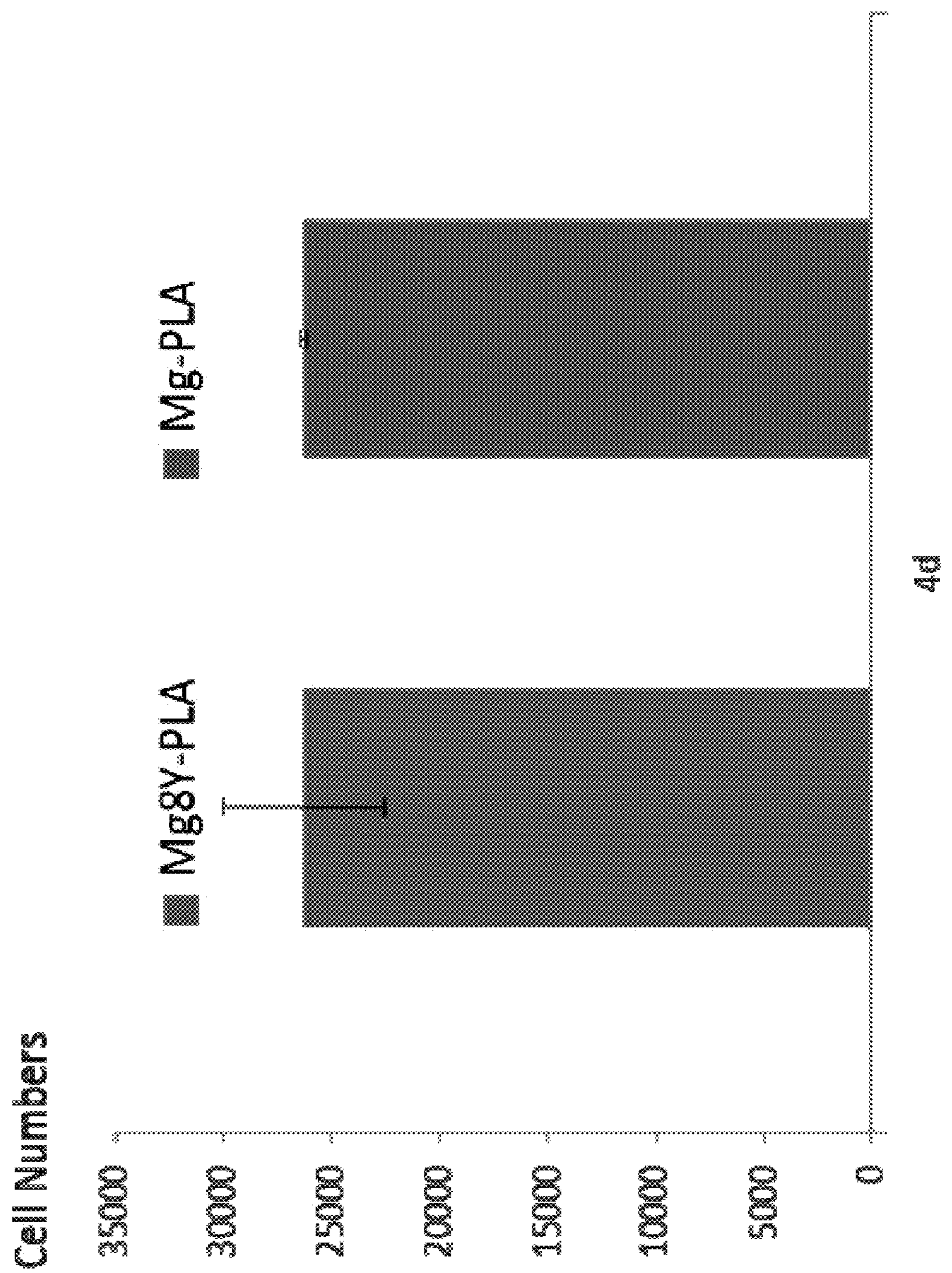
Figure 8A:
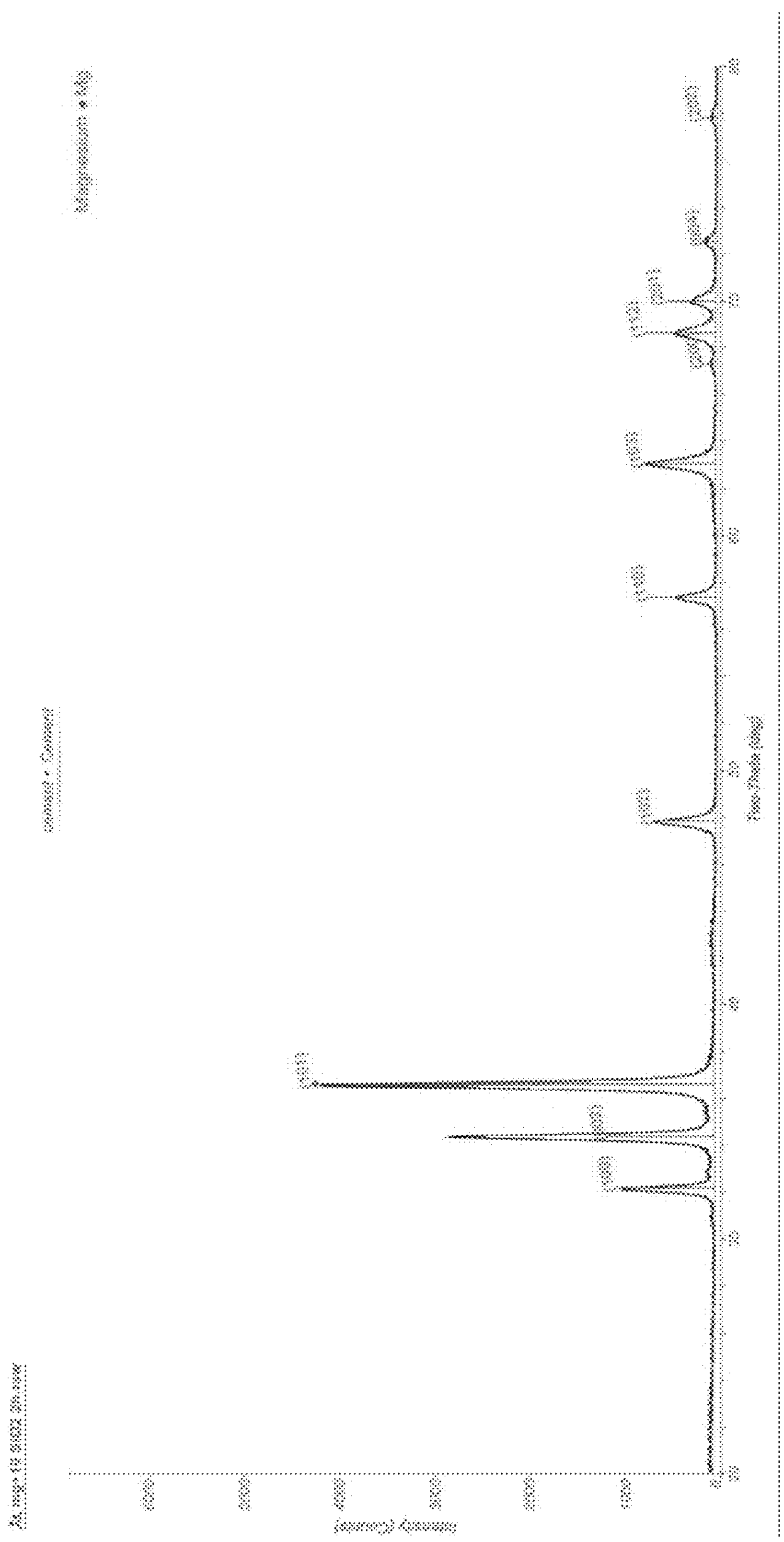
FIG. 8A shows the observed (black) versus simulated (pink) XRD pattern for the Mg—$SiO_2$ system.
Figure 8B:
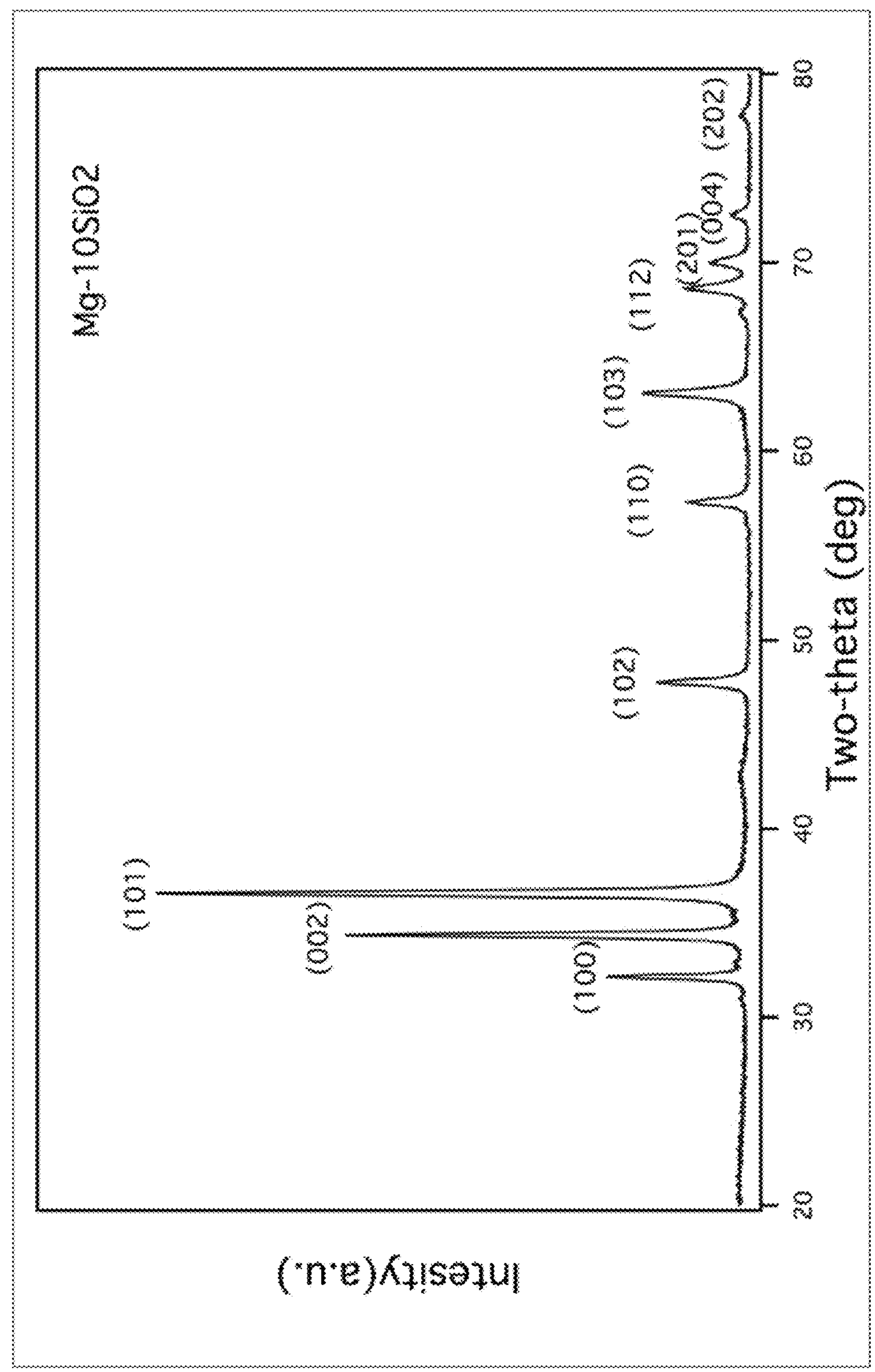
FIG. 8B shows the XRD pattern of a Mg—$SiO_2$ composite, having 10 wt % $SiO_2$, alone.
Figure 9:
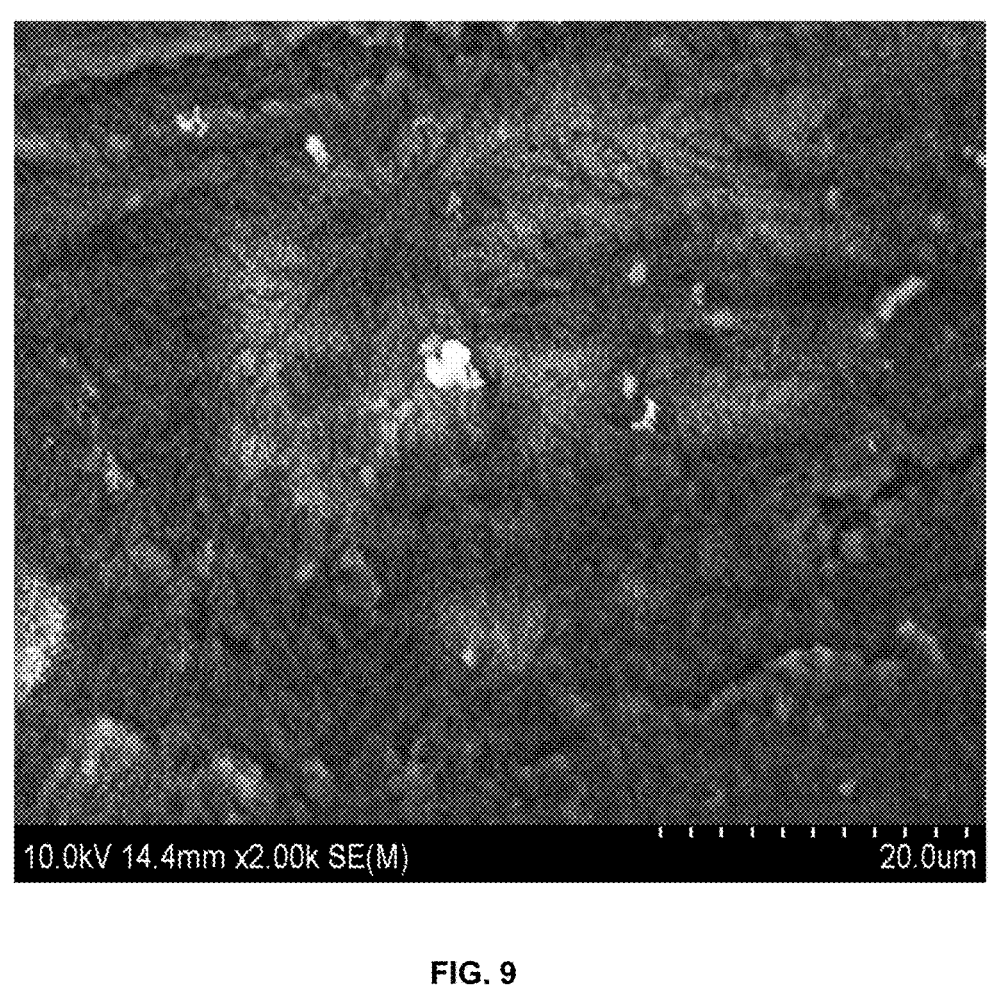
Figure 10:
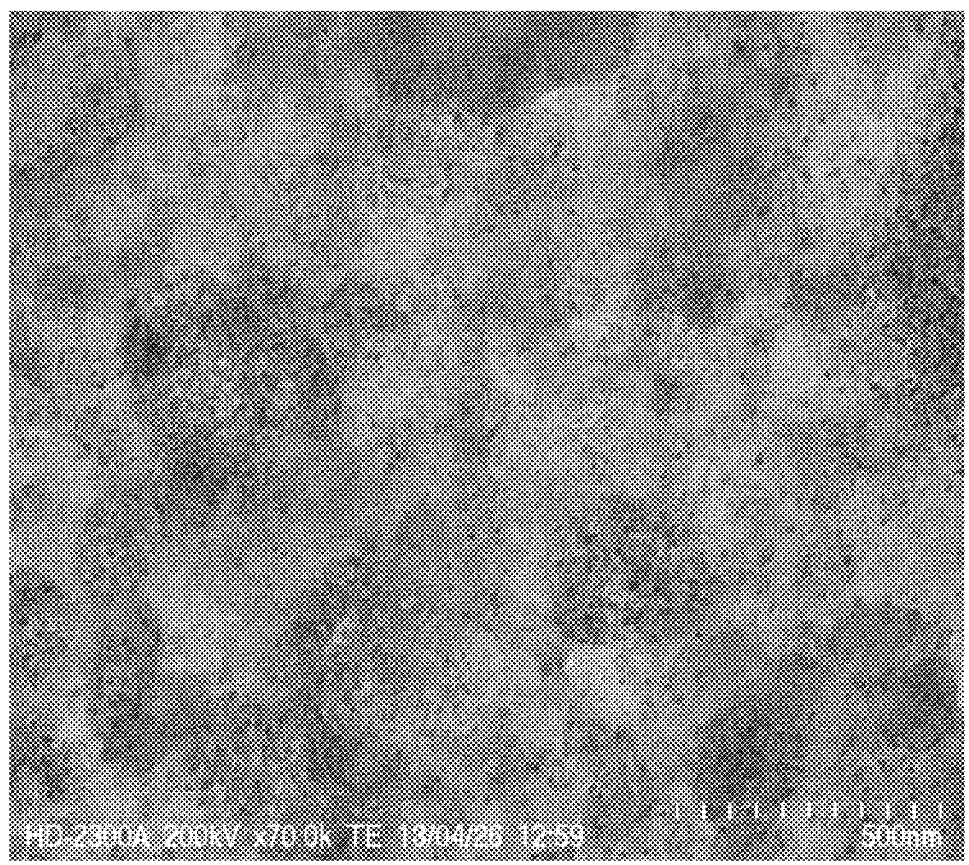
FIG. 10: TEM image of Mg—$SiO_2$ inner structure.

FIG. 4B shows a TEM image of a Mg—$SiO_2$ composite prepared from this method. FIG. 8A shows the observed XRD pattern of the Mg—$SiO_2$ system compared to the simulated pattern. FIG. 8B shows the XRD pattern of a 10 wt % silica composite prepared by this method. The Mg—$SiO_2$ composite was incubated in simulated body fluid for 90 minutes at room temperature. FIG. 9 shows a SEM image of the surface of the compound after this incubation. FIG. 10 shows a SEM image of the Mg—$SiO_2$ inner structure.

Certain embodiments of the alloys, composites, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composite comprising:

magnesium;

a rare earth element present at a concentration up to about 15 wt %; and silica present at a concentration ranging from about 10 wt % to about 15 wt %;

wherein the composite has a nanocrystalline grain size.

2. The composite of claim 1, wherein the rare earth element is not present in an oxide.

3. The composite of claim 2, wherein the rare earth element is selected from the group consisting of yttrium (Y), gadolinium (Gd), terbium (Tb), dysprosium (Dy), neodymium (Nd), lanthanum (La), cerium (Ce), praseodymium (Pr), and samarium (Sm).

4. The composite of claim 1, further comprising an additive selected from the group consisting of Ti, Al, Zr, Zn, and Mn.

5. The composite of claim 1, wherein the composite consists essentially of magnesium, yttrium, and silica.

6. The composite of claim 1, further comprising a Ca—P coating.

7. The composite of claim 6, wherein the Ca—P coating is selected from the group consisting of: hydroxyapatite ($Ca_{10}(PO_4)_6(OH)_2$), tetracalcium phosphate (TTCP, $Ca_4(PO_4)_2O$), tricalcium phosphate [$\alpha$-TCP, $\alpha$-$Ca_2(PO_4)_2$ and $\beta$-TCP, $\beta$-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), and octacalcium phosphate (OCP, $Ca_8H_2(PO_4)_6.5H_2O$).

8. An article comprising the composite of claim 1, wherein the article is selected from the group consisting of: orthopedic implants, cochlear implants, surgical staples, aneurism coils, vascular closing devices, plates, screws, intramedullary nails and pins, suture anchors, tacks, rods, anastomosis clips or plugs, dental implants, aortic aneurysm graft devices, atrioventricular shunts, heart valves, bone-fracture healing devices, bone replacement devices, endoprostheses and prostheses in the area of hard and soft tissues, joint replacement devices, tissue regeneration devices, hemodialysis grafts, indwelling arterial catheters, indwelling venous catheters, needles, vascular stents, tracheal stents, esophageal stents, urethral stents, rectal stents, stent grafts, synthetic vascular grafts, tubes, vascular aneurysm occludes, vascular clips, vascular prosthetic filters, vascular sheaths, venous valves, tubular meshes, catheters, and wires.

9. A method of controlling the degradation rate of a composite comprising:

preparing a composite of claim 1 from magnesium and silica powders through a fast densification process;

applying a Ca—P composition to the composite to form a coating; and adjusting the thickness of the coating to control the degradation rate of the composite.

10. The method of claim 9, wherein the composite is converted into bone-like apatite upon degradation.

11. A composite comprising:

magnesium;

a rare earth element comprising yttrium present at a concentration up to about 15 wt %; and silica present at a concentration ranging from about 10 wt % to about 15 wt %; wherein the composite has a nanocrystalline grain size, and the composite is porous.

* * * * *